US00RE35213E

United States Patent [19]

Floyd et al.

[11] E Patent Number: Re. 35,213

[45] Reissued Date of Patent: Apr. 16, 1996

[54] PHENYLBUTYL NITRONE COMPOSITIONS AND METHODS FOR PREVENTION OF GASTRIC ULCERATION

[75] Inventors: Robert A. Floyd, Oklahoma City, Okla.; John M. Carney, Lexington, Ky.

[73] Assignees: Oklahoma Medical Research Foundation, Oklahoma City, Okla.; University of Kentucky Research Foundation, Lexington, Ky.

[21] Appl. No.: 97,998

[22] Filed: Jul. 29, 1993

Related U.S. Patent Documents

Reissue of:

[64] Patent No.: 5,036,097
Issued: Jul. 30, 1991
Appl. No.: 491,452
Filed: Mar. 9, 1990

U.S. Applications:

[63] Continuation-in-part of Ser. No. 422,651, Oct. 17, 1989, Pat. No. 5,025,032.

[51] Int. Cl.[6] ..... A61K 31/415

[52] U.S. Cl. ..... 514/400

[58] Field of Search ..... 514/400

[56] References Cited

U.S. PATENT DOCUMENTS

| | | | |
|---|---|---|---|
| 3,296,145 | 1/1967 | Findlam et al. | 252/106 |
| 3,849,934 | 11/1974 | Dorschner et al. | 47/57.6 |
| 4,153,722 | 5/1979 | Campbell et al. | 424/304 |
| 4,197,314 | 4/1980 | Campbell et al. | 424/304 |
| 4,214,003 | 7/1980 | Campbell et al. | 424/301 |
| 4,224,340 | 9/1980 | Campbell et al. | 424/304 |
| 4,870,002 | 9/1989 | Kiel | 435/2 |

FOREIGN PATENT DOCUMENTS

87/00629 of 1988 WIPO .

OTHER PUBLICATIONS

Petkova, et al., *Agressologie* 28, 8, pp. 833–834 (1987).
Hearse, et al., *J. Mol. Cell. Cardiol.* 20, 213–223 (1988).
Bolli, et al., *J. Clin. Invest.* 82, pp. 476–485 (Aug. 1988).
Weglickl, et al., *Oxy–Radicals in Molecular Biology and Pathology*, pp. 357–364 (Proceedings of an Upjohn–UCLA Symposium Held at Park City, Utah, Jan. 24–30, 1988) Editor: Alan R. Liss, Inc., NY.
E. Masini, et al., *Agents and Actions*, vol. 27, 1/2 pp. 154–157 (1989).
Novelli, et al., *Free Radicals in Liver Injury* , pp. 225–228 (IRL Press, Oxford, England).
Novelli, et al., *Oxygen Free Radicals in Shock*, Int. Workshop, Florence 1985, pp. 119–124 (Karger, Basel 1986).
Hearse, et al., *Circulation Research* vol. 60, No. 3, pp. 375–383 (Mar. 1987).
Yanev, et al., *Oxygen Free Radicals in Shock*, Int. Workshop, FLorence 1985, pp. 193–196 (Karger, Basel 1986).
Ilieva, et al., *Neurosciences* vol. 12, pp. 223–227.
Chiu, et al., *Transplantation Proceedings* vol. XIX No. 1, pp. 1077–1079 (Feb. 1987).

(List continued on next page.)

*Primary Examiner*—Raymond Henley, III
*Assistant Examiner*—Keith MacMillan

[57] ABSTRACT

Compositions containing PBN, or active derivatives thereof, in a suitable pharmaceutical carrier for administration to a patient, are disclosed for treating or preventing gastric ulceration caused by ingestion of non-steroidal anti-inflammatories. Based on animal studies, the dosage is in the range of 3 to 300 mg/kg and is administered prior to, simultaneously, or shortly after ingestion of the NSAID compounds(s). In the preferred embodiment, the range is between 10 and 30 mg/kg, depending on the dosage unit required to protect the mucosa. The preferred method of administration is orally, alone or in combination with the non-steroidal anti-inflammatory. It is believed that the PBN is also useful alone for treatment or prevention of ulcers, aspects of diarrhea, gastritis, esophagitis, ileitis, and as an analgesic.

16 Claims, 2 Drawing Sheets

OTHER PUBLICATIONS

Hall, et al., *J. of Neurotrauma* vol. 6, 3, pp. 169–176 (1989).
Edward D. Hall, *Critical Care Clinics* vol. 5, No. 4, pp. 793805 (Oct. 1989).
Hamburger, et al., *Circulatory Shock* 29, pp. 329–334 (1989).
McKechnie, et al., *Circulatory Shock* 19, pp. 429–439 (1986).
Joe M. McCord, *The New England J. of Med.* vol. 312, No. 3, pp. 159–163 (Jan. 1985).
Chandler, et al., *J. of Pharm. Methods* 14, pp. 137–146 (1985).
Baethmann, et al., *Critical Care Medicine* vol. 16, No. 10, pp. 972–977 (Oct. 1988).
K. A. Hossman, *Critical Care Medicine* vol. 16, No. 10, pp. 964–971 (Oct. 1988).
Lars Ernster, *Critical Care Medicine* vol. 16, No. 10, pp. 947–953 (Oct. 1988).
B. K. Siesjo, *Criticla Care Medicine* vol. 16, No. 10, pp. 954–963 (Oct. 1988).
Novelli, et al., *Free Radical Biology & Medicine* 8, 9–13 (1990).
Smith, et al., *Gastroenterology* 92, 950–956 (1987).
Rainsford, *Toxicologic Pathology* 16(2), 251–259 (1988).
Rainsford, *Agents Action* 6(Suppl), 193–212 (1979).
Rainsford, Gut 16, 514–527 (1975).
Whittle and Vane, *Arch. Toxicol. Suppl.* 7, 315–322 (1984).
Kauffman and Grossman, *Gastroenterology* 75(6):1099–1102 (1978).
Hillman and Bloom, *Arch. Intern. Med.* 149, 2061–2065 (1989).
Giercksky, et al., *Scand J. Gastroenterology* "Epidemiology of NSAID–Related Gastrointestinal Side Effects" (1989).

PHENYLBUTYL NITRONE COMPOSITIONS AND METHODS FOR PREVENTION OF GASTRIC ULCERATION

Matter enclosed in heavy brackets [ ] appears in the original patent but forms no part of this reissue specification; matter printed in italics indicates the additions made by reissue.

The United States Government has certain rights in this invention by virtue of grants from the National Institutes of Health.

BACKGROUND OF THE INVENTION

This is a continuation-in-part of U.S. Ser. No. 07/422,651 entitled "Phenyl Butyl Nitrone Compositions for Treatment of Oxidative Tissue Damage" filed Oct. 17, 1989 by John M. Carney and Robert A. Floyd, *now U.S. Pat. No. 5,025,032.*

This is generally in the area of compositions and methods for use thereof for the treatment and prevention of gastrointestinal ulceration resulting from the use of nonsteroidal anti-inflammatory compounds, wherein the active compounds are phenyl butylnitrone (PBN) or derivatives thereof.

Gastric ulceration is among the most important of adverse reactions from aspirin and nonsteroidal anti-inflammatory drugs (NSAIDS). The currently accepted explanation for NSAID-induced gastric ulceration is that NSAIDS inhibit synthesis of cytoprotective prostaglandins, as reviewed by Whittle, B. R., and J. R. Vane. Arch. Toxicol. Suppl 7:315–322 (1984). This hypothesis is supported by the demonstration that exogenous prostaglandins protect from NSAID-related gastric ulcers by Graham, D. Y., et al. Lancet 2:1277–1280 (1088), but challenged by recent studies showing that NSAIDS can inhibit gastric prostaglandin production without causing ulceration, as reported by Rainsford, K. D., et al. Scand. J. Gastroenterol. 19 (Suppl 101):35–68 (1984); Ligumsky, M., et al. Gastroenterology 84:756–761 (1985); and Rainsford, K. D., "Relationship between drug absorption, inhibition of cyclo-oxygenase and lipoxygenase pathways and the development of gastric mucosal damage of non-steroidal anti-inflammatory drugs in rats and pigs". In Advances in Prostaglandins, Leukotrienes and Lipoxins. M. J. Bailey, editor. Plenum Press, New York, 639–653 (1985). Thus, the cause of NSAID-induced gastric ulceration remains controversial, as reviewed by Rainsford, K. D. Toxicologic Pathol. 16:251–259 (1988).

Free radicals have been postulated to be mediators of tissue injury including that brought on by ischemical reperfusion damage. Important production sites of the oxygen free radicals superoxide ($O_2$-) and hydroxyl (OH) radicals are the mitochondrial respiratory chain and the reaction sequences catalyzed by cyclooxygenase and lipoxygenase. However, radicals are also formed during autoxidation of many compounds (e.g., catecholamines). Ischemic events in tissue causes a spurt of free-radical formation. This may be due to oxidation of polyenoic free fatty acids, release and reuptake of catecholamines, and oxidation of xanthine and hypoxanthine by xanthine oxidase. Although all these events occur during recirculation, when the $O_2$ supply is restored after ischemia, they represent metabolic cascades triggered by agonistreceptor interactions, energy failure, and/or calcium influx during the insult. Although free radical formation is a likely cause of ischemic damage, it has been difficult to directly demonstrate that such formation occurs and/or that it is sufficiently pronounced to overwhelm the antioxidative defense of the tissue, Curran, et al., Mol. Cell. Biol. 5, 167–172 (1985). In recent years, however, evidence has been obtained that ischemia may cause conjugated dienes and malondialdehyde to accumulate in the tissue. Even so, it remains to be conclusively shown that free-radical damage to unsaturated acyl chains in phospholipids, to protein, or to nucleic acids constitutes an important role in the ischemic necrosis. At present, the evidence is relatively strong for an involvement of free-radical mechanisms in vascular injury, and in damage affecting nerve and glial cells.

Although no drugs are currently approved for clinical use in treating tissue damage due to ischemia, several compounds have been proposed as potentially being effective. Mannitol, an oxygen scavenger, has been added to reperfusion media to limit damage to organs for transplantation. Superoxide dismutase (SOD) has been suggested as a means for limiting in vivo oxidative damage. The most promising compounds that interfere with peroxidation generation are the lazaroides, modified prednisones, described by J. M. McCall, Acta Anesthesia Belgica, First Antwerp Int. Trauma Symp., which have been reported to be efficacious if given during or after ischemia. White and Aust and co-workers, Adv. Free Radical Biol. Med. 1,1–17 (1985), and Babbs, Resuscitation 13, 165–173 (1986), have demonstrated that iron chelators protect animals from ischemia/reperfusion injury.

It is therefore an object of the present invention to provide composition and methods for use thereof which are useful in preventing or treating gastric ulcers resulting from the use of non-steroidal anti-inflammatory compounds.

It is a further object of the present invention to provide compositions and methods for use thereof which are useful in preventing or treating pain and fever in vivo resulting from infection and inflammation.

SUMMARY OF THE INVENTION

Compositions containing PBN, or active derivatives thereof, in a suitable pharmaceutical carrier for administration to a patient, are disclosed for treating or preventing gastric ulceration caused by ingestion of non-steroidal anti-inflammatories. The compositions have the following general formula:

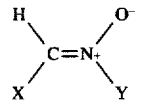

wherein:

X is phenyl or

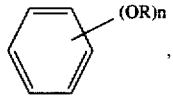

wherein R is H,

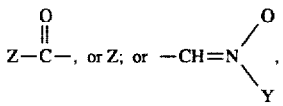

and n is a whole integer from 1 to 5; or

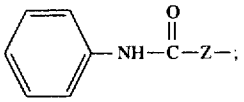

Y is a tert-butyl group that can be hydroxylated or acetylated on one or more positions; phenyl; or

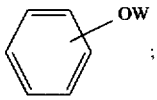

wherein W is

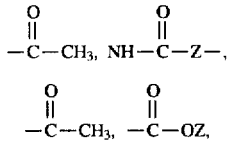

or Z; and

Z is a $C_1$ to $C_5$ straight or branched alkyl group.

Based on animal studies, the dosage is in the range of 3 to 300 mg/kg and is administered prior to, simultaneously, or shortly after ingestion of the NSAID compound(s). In the preferred embodiment, the range is between 10 and 30 mg/kg, depending on the dosage unit required to protect the mucosa. The preferred method of administration is orally, alone or in combination with the non-steroidal anti-inflammatory. It is believed that the PBN is also useful alone for treatment or prevention of ulcers, aspects of diarrhea, gastritis, esophagitis, ileitis, and possibly pain and fever in a manner analogous to analgesics such as aspirin and acetaminophen.

DETAILED DESCRIPTION OF THE INVENTION

Figure 1:
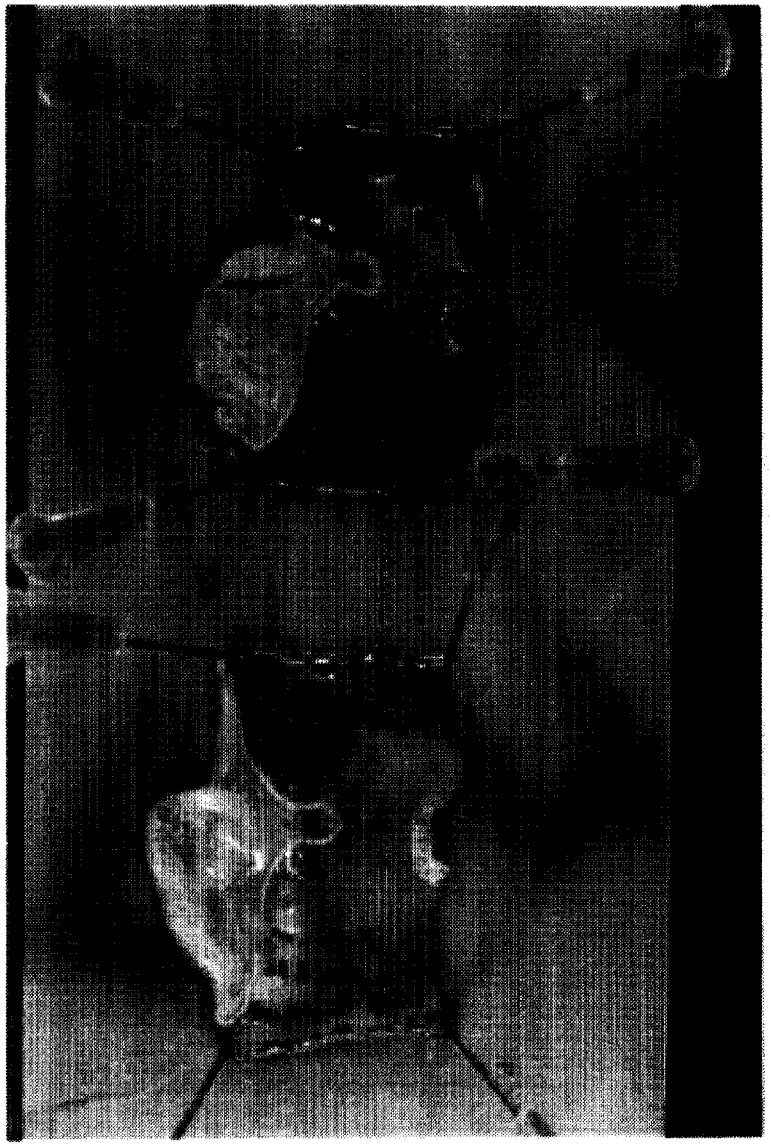
FIG. 1 is a comparison of the stomach from a piroxicam treated rat (right) to the stomach from a vehicle control treated rat (left). Piroxicam at 23 mg/kg caused prominent ulceration along the ridges of gastric rugae.

Gastric parietal cells have abundant mitochondria to generate the energy required for hydrogen ion secretion. Salicylate and NSAIDS have long been recognized as uncouplers of mitochondrial oxidative phosphorylation, and aspirin decreases mucosal adenosine triphosphate (ATP) and phospbhocreatine (PC) in isolated perfused gastric mucosa. Thus, aspirin and NSAIDS might be expected to produce changes in the energy state of gastric mucosa similar to those caused by ischemia, when ATP is depleted and then degraded to hypoxanthine, as discussed by McCord, J. M. N. Engl. J. Med. 312:158–163 (1985). Xanthine oxidase-mediated ischemia-reperfusion injury of the stomach has recently been reported as a cause of stress ulceration in hemorrhagic shock, as reported by Itoh, M., and P. H. Guth. Gastroenterology 88:1162–1167 (1985); Perry, M. A., et al. Gastroenterology 90:362–367 (1986); and Smith, S. M., Gastroenterology 92:950–956 (1987). If aspirin and NSAIDS impair mitochondrial energy metabolism, the subsequent breakdown of high energy purines to xanthine might also stimulate xanthine oxidase-mediated oxidant injury in gastric mucosa, resulting in ulceration.

It has now been discovered that, further to the methods using PBN for the treatment and prevention of ischemic damage, including by decreasing or preventing ATP depletion, described and claimed in U.S. Ser. No. 07/422,651 filed Oct. 17, 1989, PBN, and derivatives thereof having spin-trapping activity, are useful in preventing or treating gastric ulceration resulting from ingestion of non-steroidal anti-inflammatories. As used herein, a free radical scavenger or spin-trap reagent is a molecule that will form a stable complex with a free radical. A free radical carbon trap is a molecule in which the free radical is localized on a carbon atom or a nitrogen atom. As a result of this chemical bond formation, the free radical is no longer damaging to the cell.

α-phenyl t-butyl nitrone (PBN), and derivatives thereof, in a pharmaceutical vehicle suitable for administration to a patient, preferably by oral administration, are useful in preventing or reversing gastric ulceration caused by the use of non-steroidal anti-inflammatories (NSAID). PBN has a number of advantages in the treatment of gastric ulceration, especially its complete lack of a measurable effect on normal or uninjured cells. PBN is the preferred active compound at this time, although a number of derivatives are also useful, including hydroxy derivatives, especially 2-, 3- or 4-hydroxy PBN and mono-, di- and trihydroxy tert-butyl nitrone; esters, especially esters which release 2-, 3, or 4-hydroxyphenyl t-butyl nitrone such as the acetoxy derivative, 2-, 3-, or 4-carboxyphenyl t-butyl nitrone, such as the ethyl derivative, or phenyl hydroxybutyl nitrone, such as the acetoxy derivative; alkoxyl derivatives, especially lkoxyl derivatives which release 2-, or 4-hydroxyphenyl t-butyl nitrone, such as the methyl derivative; and acetamide derivatives, especially acetamide derivatives which release 2-, or 4 aminophenyl t-butyl nitrone, such as the acetyl derivative; diphenyl nitrone (PPN) and the analogous diphenyl nitrone derivatives. As used herein, "PBN" refers to both α-phenyl t-butyl nitrone and derivatives thereof, unless otherwise stated. The active agent in the compositions is N-tert-Butyl-α-phenylnitrone (PBN) or derivatives thereof that are spin trap reagents and in addition to chemical binding of free radicals, may also act to prevent ATP depletion of cells.

The general formula for PBN and useful derivatives thereof is:

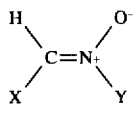

wherein:

X is phenyl or

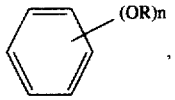

wherein R is H,

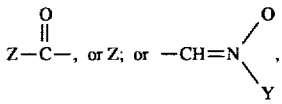

and n is a whole integer from 1 to 5; or

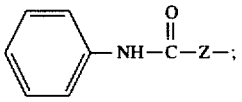

Y is tert-butyl group that can be hydroxylated or acetylated on one or more positions; phenyl; or

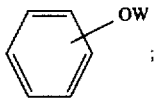

wherein W is

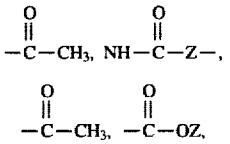

or Z; and

Z is a $C_1$ to $C_5$ straight or branched alkyl group.

The compositions can also contain other active agents, such as buffering agents such as antacids or inert carriers such as lactose. Examples of commonly used NSAIDs include aspirin, acetaminophen, ibuprofen, piroxicam, naphroxen, flufenamic and methanamic acid and related nonsteroidal antiinflammatory compounds.

Examples demonstrate the utility of the compositions in preventing or treating ulceration resulting from ingestion of NSAIDs. Exemplary dosages of PBN ranged from 3 to 300 mg/kg of body weight in animals. The effective range of PBN in humans and other mammals is expected to be between approximately 10 and 300 mg/kg, preferably between 10 and 30 mg/kg body weight. The compositions can be effectively administered prior to, during or shortly after ingestion of NSAIDs, and prevent or decrease the extent of cellular damage.

Since the trapping of endogenous free radicals is specific for only those cells that have been exposed to the conditions that result in the production of free radicals, the traps have little or no effect on normal cells. The beneficial effects occur only in injured cells, and do not require the presence of specific receptors, specific enzymes, and/or specific cell types.

The PBN is preferably administered systemically, most preferably orally, since this is the most rapid and efficient means for delivering the active compound to the site of free radical generation. The PBN may be administered at once, or may be divided into a number of smaller doses to be administered at varying intervals of time. Other methods of administration can also be used, including subcutaneous, intravenous, and intraperitoneal administration. The pharmaceutical compositions should provide a dosage of PBN relative to the dosage of NSAID sufficient to protect the mucosa from the effect of the NSAID. The concentration of active compound in the drug composition will depend on absorption, inactivation, and excretion rates of the drug as well as other factors known to those skilled in the art. The compositions are administered prior to, at the same time as, or shortly after ingestion of the non-steroidal anti-inflammatories. The effective dosage may also be determined based on that amount required to prevent or reverse predisposition of the cells to damage resulting from depletion of ATP (as demonstrated by in vivo NMR) and damage from free radical generation. It is to be noted that dosage values will also vary with the condition of the patient being treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition.

A preferred mode of administration of the active compound is in a form for oral delivery. Oral compositions will generally include an inert diluent or an edible carrier. Preferred pharmaceutical carriers for intravenous administration are saline or phosphate buffered saline at physiological pH. Since PBN degrades at pH less than approximately 3 to 4, it is preferred to administer the PBN at a pH of 4 or higher, or in combination with food or a buffering agent. For oral delivery, the PBN may be enclosed in capsules, compressed into tablets, microencapsulated, entrapped in liposomes, in solution or suspension, alone or in combination with a substrate immobilizing material such as starch or poorly absorbable salts such as immodium. Pharmaceutically compatible binding agents, and/or adjuvant materials can be included as part of the composition. The tablets or, capsules may contain, for example, any of the following ingredients, or compounds of a similar nature: a binder such as microcrystalline cellulose, gum tragacanth or gelatin; an excipient such as starch or lactose, a disintegrating agent such as alginic acid, Primogel®, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The present invention will be further understood with reference to the following non-limiting examples demonstrating methods for determining effectiveness of PBN administration for treatment or prevention and/or reversal of damage from NSAIDs.

EXAMPLE 1: COMPARISON OF PIROXICAM-INDUCED ULCER WITH CONTROL.

The following materials and methods were used in examples 1 and 2.

Animal Experiments.

Male Sprague-Dawley rats (Charles River, Wilmington, Mass.) weighing 300–325 g were housed individually in wire bottomed cages to prevent ingestion of hair and feces. Animals were maintained without food for 48 hours and without water for 24 hours prior to each experiment. Piroxicam or aspirin and other NSAIDS were suspended in a vehicle of 1% carboxymethylcellulose, 0.1% Tween 80 and 0.15 M HCl, and administered in a volume of 1 ml on the morning of study by oral gavage using an 18 gauge curved blunt needle (Popper and Sons, New Hyde Park, N.Y.). One ml of vehicle alone was administered for control experiments. HCl was added to the vehicle to insure an acid environment in the stomach in all studies. Preliminary experiments showed that 23 mg/kg piroxicam consistently produced ulceration, and this dose was used in all subsequent studies. Four hours after the administration of NSAID or vehicle, rats were euthanized with sodium pentobarbital (100 mg/kg IP), and the surface area of ulceration per stomach was quantitated using morphometric techniques. Stomachs were removed, the lumen was exposed by an incision along the radius of greater curvature, and the stomach was washed in phosphate buffered saline. The luminal surface was laid out on a flat surface with gross folds removed by gentle distension. The percentage of surface involved with submucosal hemorrhage was then determined by point counting, as described by Weibel, E. R. Stereological Methods: Practical Methods for Biological Morphometry. Academic Press, New York 1980. This was done by tabulation of the percentage of points over ulcerations using a point counting eyepiece graticle (16×16 points in a square format). At the 22× magnification used on the Wild dissecting microscope (Wild-Heerbrugg, Basel, Switzerland), the graticle covered a 1 $cm^2$ area of the surface. Four to five non-overlapping sampling sites were taken to fully cover the exposed surface. To determine the total luminal surface area, the outline of the outer boundary of the stomach was traced using a transparent acetate sheet, and the area was determined from planimetry. The surface area of ulcerated regions per stomach was then determined by multiplying the surface density of ulceration regions by the luminal surface area of the stomach.

MEASUREMENT OF LIPID PEROXIDATION IN STOMACHS.

Lipid peroxidation is studied in piroxicam-and vehicle-treated rat stomachs by measuring thiobarbituric acid (TBA) reactivity of gastric punch biopsies by the method of Buege and Aust Buege, J. A., Aust, S. D. Methods Enzymol 51:302–310 (1978). Four hours after piroxicam or vehicle, stomachs are opened along the radius of greater curvature, washed with ice cold normal saline, and spread along a flat surface with lumens exposed. Five punch biopsies from mucosal through serosal surfaces are taken from each stomach using a 3 mm diameter skin biopsy punch. Biopsies are taken over ulcers in piroxicam treated stomachs and randomly over gastric rugae (where ulcers occur) in vehicle control stomachs. Biopsies from each stomach are combined, homogenized on ice in 1 ml of cold 1.15% KCl, and mixed with 2 ml of TBA reagent (0.375% thiobarbituric acid and 15% trichloroacetic acid in 0.25 HCl, to which 0.01% butylated hydroxytoluene is added just prior to use). After incubation at 100° C. for 15 minutes, the mixture is cooled and centrifuged at 1,500 g for 10 min. The absorbance of the supernatant is measured at 532 nm, and results expressed as $A_{532}$ per stomach.

MEASUREMENT OF GLUTATHIONE IN GASTRIC MUCOSA.

Gastric mucosal glutathione is measured in piroxicam- and vehicle-treated rat stomachs. Four hours after piroxicam or vehicle, stomachs are opened, washed with ice cold saline, and spread along a flat surface with lumens exposed. The gastric mucosa is then removed by scraping with a surgical blade. The mucosa is homogenized on ice in 1 ml of 1.15% KCl. Two aliquots of 250 μl are snap frozen in liquid nitrogen and stored at −70° C. for later determination of total glutathione by the method of Anderson, M. E. Methods Enzymol 113:548–555 (1985) and protein by a modification of the Lowry method, described by Bennett, J. P. Techniques Lipid Membrane Biochem. B408:1–22 (1982), using bovine serum albumin as a standard. Results are expressed as nmole/mg protein. To measure oxidized glutathione (GSSG), the remaining 500 μl is mixed with an equal volume of N-ethylmaleimide (NEM) in water (10 mM final concentration of NEM), snap frozen and stored at −70° C. After thawing for analysis, this mixture is passed over at C-18 Sep-Pak column (Waters Associates, Milford, Mass.) and washed with 1 ml phosphate buffer (pH 7.5). This technique for removing excess NEM has been previously shown to result in >90% recovery of GSSG. GSSG is then assayed by the method used above to determine total glutathione.

MEASUREMENT OF GASTRIC XANTHINE OXIDASE ACTIVITY.

Xanthine dehydrogenase (XDH) and oxidase (XO) activities are measured in whole stomach from piroxicam-treated and vehicle-treated rats, using methods reported by Parks, et. al. Am. J. Pathol. 254 (Gastrointest Liver Physiol 17): G768–G774 (1988). The artifactual conversion of XDH to XO is minimized by quickly removing stomachs from rats that were anesthetized with 50 mg/kg sodium pentobabital and still breathing spontaneously. After gastrectomy, the rats are euthanized by cutting the abdominal aorta. Stomachs are quickly rinsed in an ice cold homogenizing buffer consisting of 50 mM potassium phosphate buffer, pH 7.0, containing 10 mM dithiothreitol (DTT), 1 mM phenylmethylsulfonyl fluoride (PMSF) and 0.1 mM EDTA. The stomach is then immediately immersed in liquid nitrogen and ground to a fine powder under liquid nitrogen using a mortar and pestle. About 0.5 g of frozen powder is added to 5 ml of homogenizing buffer and centrifuged 40,000 g for 30 min. The supernatant is decanted and microfuged for an additional 10 min. Supernatants are not stored but assayed less than 2 hours after collection to prevent loss of activity.

The spectrophotometric assay used is based on production of uric acid at 295 nm ($lambda_{295}$=1.1 z $10^4 M^{-1} cm^{-1}$). To increase reaction rates activity was measured at 30 rather than 25° C. One ml reaction mixtures contained 500 μl sample, 50 μM xanthine and 100 μM EDTA in 50 mM potassium phosphate buffer, pH 7.8 XO is assayed in the absence in NAD+, while XDH +XO activity is measured in the presence of 500 μM NAD+. Enzyme activities are reported as international units (1 μmol of urate formed per min.). The extent of XDH conversion (% XO) is calculated from XO activity divided by XDH+XO activity.

Studies of Mitochondrial Respiration.

Rat liver mitochondria are prepared using the method of Lai and Clark Methods Enzymol 55:51–60 (1979). The livers are excised rapidly into ice cold isolation medium containing 0.25M sucrose, 10 mM tris(hydroxymethyl)aminomethane (Tris), 0.25% bovine serum albumin (fatty acid free), and 0.5 mM potassium EDTA, pH 7.4. The tissue is minced and rinsed three times in cold isolation medium. The minced tissue is placed in a Dounce homogenizer with 20 ml cold isolation medium, gently homogenized, and diluted with an additional 10 ml of isolation medium. The homogenate is centrifuged at 2,000 g for 3 min., and the resulting supernatant recentrifuged at 12,500 g for 8 min. The crude mitochondrial pellet is suspended in 0.12M mannitol-0.03M sucrose medium containing 3% Ficoll, gently layered onto 20 ml of 6% Ficoll (0.25M mannitol-0.06M sucrose), and centrifuged at 11,500 g for 30 min. The resulting mitochondrial pellet is resuspended in the isolation medium and recentrifuged for 10 min. at 12,000 g. The final pellet is brought to a concentration of 10 to 15 mg of mitochondrial protein per ml with isolation medium. Mitochondrial protein is determined by the Biuret reaction described by Gornall, A. G., et al. Biol Chem 177:751–766 (1949), using bovine serum albumin as a standard. Mitochondrial respiration is measured polarographically in a magnetically stirred chamber at 25° C., using a Clark microelectrode (Diamond Electro-tech, Ann Arbor, Mich.). The incubation medium contains the following (in mM): 5K+, 226 mannitol, 75 sucrose, 5 Tris-phosphate, 10 Tris-Cl, and 0.05 EDTA at pH 7.4. State 4 respiratory rates are determined using both NADH-linked (2.5 mM malate+2 mM glutamate) and $FADH_2$-lined (10 mM succinate) substrates, with 5 mM KCl at pH 7.0. State 3 respiration rates are measured after stimulation with 1.5 mM ADP. Respiratory control ratios are determined as the ratio of State 3 to State 4 respiration after incubation with 0, 50, 100 and 200 μM piroxicam.

Studies of Microsomal Lipid Peroxidation.

Microsomes are isolated from rat livers by modification of the method of Fleisher and Kervina, Methods Enzymol 31:7–41 (1974). Rats are euthanized by $CO_2$ narcosis. The livers are excised rapidly into cold isolation medium containing 0.1M sodium phosphate and 2 mM EDTA, pH 7.4. The tissue is minced and homogenized in 3 ml isolation medium per gram of tissue using a Potter-Elvehjam homogenizer. The homogenate is centrifuged at 17,800 g for 20 min., and the pellet discarded. The supernatant is recentrifuged at 100,000 g for 60 min. The resulting pellet is resuspended in isolation buffer and recentriguged at 100,000 g for 40 min. The final pellet is resuspended in storage buffer containing 100 mM potassium phosphate, 20% glycerol, 1 mM EDTA, 1 mM DTT and 20 μM butylated hydroxytoluene, pH 7.25. This suspension is frozen under liquid nitrogen and stored at −70° CL until use. Microsomal protein is determined by a modification of the Lowry method of Anderson, M. E. Methods Enzymol 113:548–555 (1985). The effect of 200 μM piroxicam on microsomal lipid peroxidation is studied by incubating 1 mg microsomal protein in 100 mM potassium phosphate, pH 7.25, on a shaking water bath at 37° CL for 90 min., with and without the addition of 2 mM NADPH or 1 mM EDTA. Lipid peroxidation in the 1 ml reaction mixture is measured by mixing with 2 ml TBA reagent and assaying for thiobarbituric acid reactivity by the method of Buege and Aust. Values are expressed as the increase in absorbance at 532 nm ($A_{532}$) per mg microsomal protein and represent the mean of three replicates.

Statistical Analysis.

Differences in total luminal surface area in $cm^2$, surface area of ulcerated regions per stomach and bio-chemical analyses between each treatment intervention and its corresponding untreated control group are compared using the Mann-Whitney U Test, Dixon, W. J., Massey, F. J., Jr. Introduction to statistical methods, 4th edition. (New York: McGraw Hill, 1983). The effect of treatment interventions on NSAID-induced ulceration are displayed graphically as % of control ulceration, determined by summing the ratios of $cm^2$ ulceration in each treatment stomach to the mean $cm^2$ ulceration of respective untreated NSAID control stomachs, and multiplying +100. In vitro studies are compared using the Student's unpaired T-test, Dixon, W. J., Massey, F. J., Jr. Introduction to statistical methods, 4th edition. (New York: McGraw Hill, 1983). Values are expressed as mean±SEM. Significance is assumed when $P<0.05$.

Reagents and Pharmaceuticals

Phenyl N-tert-butyl nitrone is obtained from Aldrich Chemicals, Milwaukee, Wis. All other chemicals and pharmaceuticals are from Sigma Chemical. Piroxicam caused profound gastric ulceration. FIG. 1 shows that piroxicam-induced ulcers usually occurred only on the ridges of gastric rugae and spread linearly along these ridges, without involvement of the remaining gastric surface area. In the absence of an intervention, a mean of 0.215 $cm^2$ ulceration was present in piroxicam-treated control stomachs. However, the degree of ulceration in this highly stress-dependent model was variable, ranging among experiments from 0.03±0.009 to 0.706±0.104 $cm^2$. For this reason, each treatment intervention was compared to its own group of control rats that were fasted simultaneously and treated with piroxicam at the same time.

EXAMPLE 2: SUPPRESSION OF PIROXICAM-INDUCED ULCERS BY FREE RADICAL SCAVENGERS.

Piroxicam was selected as a model NSAID because it is highly ulcerogenic in rats and mice, yet is a relative weak reversible inhibitor of prostaglandin synthesis. The spin trap phenylbutyl nitrone (PBN) was used to explore the role of free radicals and oxidative events mediated by xanthine oxidase- and iron-mediated oxidant injury in the pathogenesis of piroxicam-induced gastric ulcers. In each experiment, the surface area of gastric ulceration produced by piroxicam in 15 treated rats was compared to that in 15 rats of the same age and size that were fasted simultaneously but which received no intervention. Phenylbutyl nitrone (30 mg/kg) was given orally in water 1 hour before piroxicam and also added to vehicle when piroxicam was administered. When intervention were given with piroxicam, the pH of the final mixture was adjusted if necessary to equal that of piroxicam and vehicle alone.

To generalize the findings relative to piroxicam to other NSAIDS, the effect of PBN, administered as above, can be compared with the effect on gastric ulceration from aspirin (200 mg/kg), diflunisal (125 mg/kg), naproxen (150 mg/kg) and ibuprofen (230 mg/kg).

Figure 2:
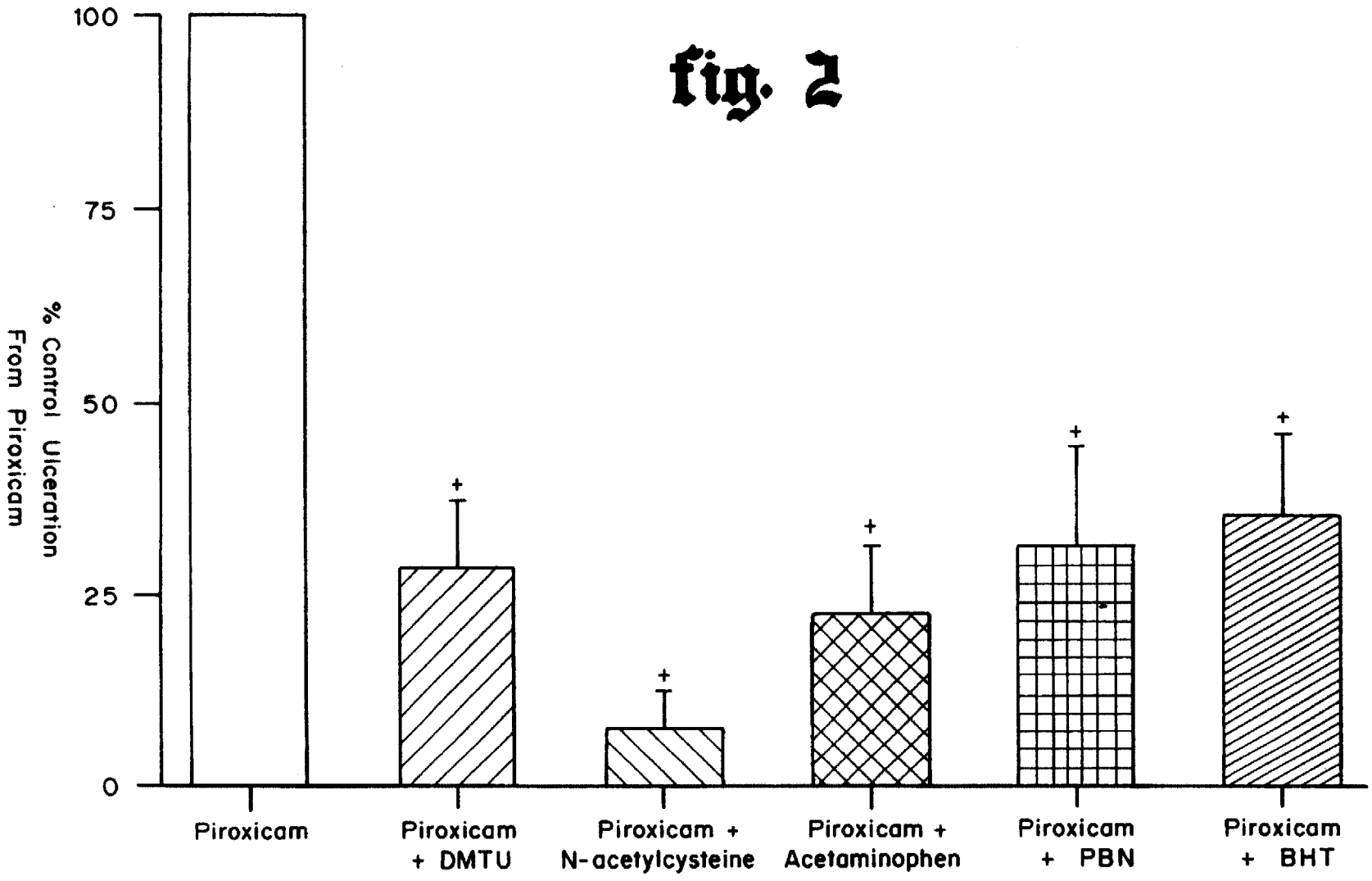
FIG. 2 is a graph of % control ulceration from piroxicam versus the % ulceration in the presence of free radical scavengers. The sulfhydryl scavenger dimethylthiourea (DMTU), 500 mg/kg i.p.) was given 24 hours and 1 hour before piroxicam. The sulfhydryl scavenger N-acetylcysteine (300 mg/kg), the hydroquinone acetaminophen (400 mg/kg) and the spin-trap phenylbutyl nitrone (PBN, 30 mg/kg) were given orally 1 hour before and along with piroxicam. The antioxidant butylated hydroxytoluene (BHT, 25 mg/kg/day i.p. in corn oil) was given for three days before and again 1 hour before piroxicam. The % control ulceration is determined by averaging the ratios of $cm^2$ ulceration in control stomachs from rats given piroxicam alone, and multiplying×100. +P<0.01 compared to piroxicam alone.

Piroxicam-induced ulcers were markedly reduced in rats treated with free radical scavengers, as shown in FIG. 2, suggesting that generation of reactive oxygen species is an important mechanism in the pathogensis of piroxicam-induced ulcers. In ulcerations/unit area, piroxicam only produced 0.229±0.145 ulcerations/unit area, and piroxicam plus PBN produced 0.077±0.104 ulcerations/unit area, statistically significant at $p<0.0052$. In contrast, ascorbate, a reducing substance that is well-recognized to facilitate iron-dependent generation of reactive oxygen species, increased ulceration by over 600% compared to control stomachs treated with piroxicam alone (0.194±0.039 $cm^2$ ulceration in ascorbate-treated stomachs vs 0.031±0.009 $cm^2$ in stomachs receiving piroxicam alone, P<0.001. In support of an oxidant mechanism as the pathogenesis of ulcers from piroxicam, thiobarbituric acid reactivity was significantly increased in gastric biopsies from piroxicam treated rats compared to rats treated with vehicle alone ($A_{532}$=0.104±0.010 for piroxicam vs 0.075±0.004 for vehicle treated stomachs, P<0.05). Piroxicam also decreased total glutathione in gastric mucosa (0.33±0.03 nmoles/mg protein) compared to vehicle alone (0.042±0.07 nmoles/mg protein) and increased the fraction of GSSG (8.9±0.9 for piroxicam vs 6.4 0.7% for vehicle), although these differences failed to achieve statistical significance.

Xanthine oxidase activity was readily identified in whole stomach. Piroxicam treated stomachs had 30.5±1.6 mU/g of total XHD+XO activity, of which 45±3% was XO. Vehicle treated control stomachs had 31.6±2.45 mU/g X. Piroxicam increases the rate of mitochondrial oxygen uptake in the absence of ADP (State 4) and that normal stimulation of respiration by ADP (State 3) is lost in the presence of piroxicam. This inhibition of respiratory control by piroxicam was demonstrated for both $FADH_2$-linked and NADH-linked substrates. However, piroxicam did not increase generation of $O_2$-by mitochondrial respiration. Piroxicam had no effect on NADPH-dependent microsomal lipid peroxidation.

Aspirin (0.972±0.318 $cm^2$), diflunisal (0.597±0.103 $cm^2$), naproxen (0.370±0.056 $cm^2$) and ibuprofen (0.644±0.110 $cm^2$) also caused severe gastric ulceration. In summary, ulceration from piroxicam was markedly inhibited by the spin-trap PBN.

EXAMPLE 3: NON-TOXICITY OF PBN AND BIOAVAILABILITY.

Previous studies on mutagenicity using standard techniques have demonstrated that PBN and analogs thereof are not mutagenic. In addition, in vitro cytotoxicity tests using human lymphocytes have indicated that PBN in concentrations of up to at least 100 μmolar have no cytotoxic effect.

In vivo toxicity tests have indicated the following. Acute doses PBN in doses up to 3 g/kg in rodents have no adverse effects. An $LD_{50}$ has yet to be determined because of the lack of toxicity. Acute i.v. doses of PBN ranging from 10 to 300 mg/kg body weight (injected within 60 seconds) have no acute toxic effects in gerbils. Continuous i.v. administration of PBN at a dose of 50 mg/kg/hr for a total of 48 hr has no adverse effect on gerbils.

An estimate of the bioavailability of PBN demonstrates that it is widely available throughout the body and is able to cross all of the barriers to distribution, including the blood brain barrier (the brain shows 80% of the plasma concentration). Limited pharmokinetic studies indicate that the plasma half-life in the rat is three to four hours.

Modifications and variations of the present invention, compositions containing PBN and derivatives thereof, and methods using the compositions for the treatment or prevention of gastric ulceration resulting from ingestion of non-steroidal anti-inflammatories, will be obvious to those skilled in the art from the foregoing detailed description. Such modifications and variations are intended to come within the scope of the following claims.

We claim:

1. A method for in vivo treatment or prevention of gastric ulceration from ingestion of non-steroidal antiinflammatories comprising:

administering to a patient in need of such treatment α-phenyl t-butyl nitrone [and derivatives] *or a derivative* thereof [having spin-trapping activity and preventing ATP depletion in vivo in tissue] having the formula:

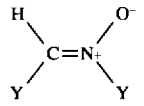

wherein:

X is phenyl or

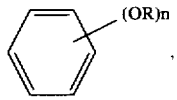

wherein R is H,

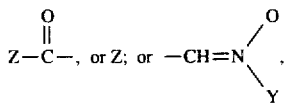

and n is a whole integer from 1 to 5; or

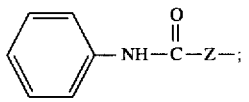

Y is a tert-butyl group that can be hydroxylated or acetylated on one or more positions; phenyl; or

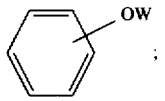

wherein W is

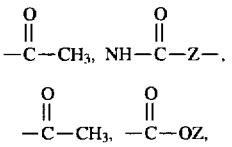

or Z; and

Z is a $C_1$ to $C_5$ straight or branched alkyl group; and a pharmaceutically acceptable carrier for oral administration to a patient, in a dosage effective to treat or prevent gastric ulceration from ingestion of nonsteroidal anti-inflammatory compounds.

2. The method of claim 1 wherein the phenyl butyl nitrone derivatives are selected from the group consisting of hydroxy PBNs, PBN esters, acetoxy PBNs, alkyl PBNs, alkoxyl PBNs, phenyl PBNs.

3. The method of claim 1 wherein the PBN derivative is functionalized to release in vivo a compound selected from the group consisting of 2-, 3-, and 4-hydroxyphenyl t-butyl nitrone; 2-, 3-, and 4-hydroxyphenyl t-butyl nitrone; 2-, 3-, 4-carboxyphenyl t-butyl nitrone; and 2-, 3-, and 4-aminophenyl t-butyl nitrone.

4. The method of claim 1 comprising as the active ingrdient α-phenyl t-butyl nitrone.

5. The method of claim 1 wherein the PBN [and derivatives] *or a derivative* thereof is in a pharmaceutical carrier delivering an effective dosage to a patient to treat or prevent gastric ulceration from simultaneous ingestion of nonsteroidal antiinflammatory compounds.

6. The method of claim 1 wherein the PBN [and derivatives] *or a derivative* thereof is in a pharmaceutical carrier delivering an effective dosage to a patient to treat or prevent gastric ulceration from subsequent ingestion of non-steroidal anti-inflammatoriy compounds.

7. The method of claim 6 wherein the non-steroidal anti-inflammatory is selected from the group consisting of aspirin, acetaminophen, ibuprofen, piroxicam, naproxen, flufenamic and methanamic acid and related nonsteroidal antiinflammatory compounds.

8. The method of claim 1 wherein the PBN [and derivatives] *or a derivative* thereof is provided in a dosage of between 3 and 300 mg PBN/kg body weight.

9. The method of claim 8 wherein the PBN[and derivaties] *or a derivative* thereof is provided in a dosage of between 10 and 30 mg/kg body weight.

10. The method of claim 1 wherein the PBN [and derivatives] *or a derivative* thereof is provided in combination with a pharmaceutical carrier selected from the group consisting of microcapsules, liposomes, immobilizing substrates, salts that are poorly absorbed through the gastrointestinal lining, oils, and buffering agents.

11. A composition for in vivo treatment or prevention of gastric ulceration comprising:

α-phenyl t-butyl nitrone [and derivatives] *or a derivative* thereof [having spintrapping activity and preventing ATP depletion in vivo in tissue] having the formula:

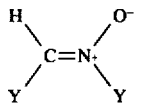

wherein:

X is phenyl or

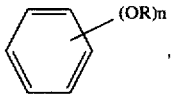

wherein R is H,

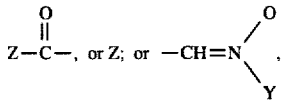

and n is a whole integer from 1 to 5; or

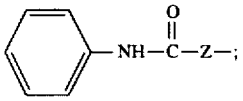

Y is a tert-butyl group that can be hydroxylated or acetylated on one or more positions; phenyl; or

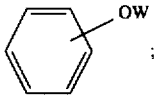

wherein W is

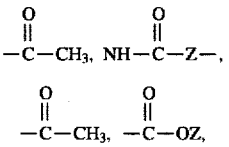

or Z; and

Z is a $C_1$ to $C_5$ straight or branched alkyl group; and a pharmaceutically acceptable carrier for oral administration to a patient, wherein the α-phenyl t-butyl nitrone [and derivatives] *or a derivative* thereof is in a dosage effective to prevent or treat gastric ulceration by non-steroidal antiinflammatory compounds wherein the PBN [and derivatives] *or a derivative* thereof is in combination with a non-steroidal anti-inflammatory, said agents being present in effective amounts.

12. The composition of claim 11 wherein the phenyl butyl nitrone derivatives are selected from the group consisting of hydroxy PBNs, PBN esters, acetoxy PBNs, alkyl PBNs, alkoxyl PBNs, phenyl PBNs.

13. The composition of claim 11 wherein the PBN derivative is functionalized to release in vivo a compound selected from the group consisting of 2-, 3-, and 4-hydroxyphenyl t-butyl nitrone; 2-, 3-, and 4-hydroxyphenyl t-butyl nitrone; 2-, 3-, and 4-carboxyphenyl t-butyl nitrone; and 2-, 3-, and 4-aminophenyl t-butyl nitrone.

14. The composition of claim 11 comprising as the active ingredient α-phenyl t-butyl nitrone.

15. The composition of claim 11 wherein the PBN [and derivatives] *or a derivative* thereof is in a pharmaceutical carrier delivering an effective dosage to a patient to prevent injury from simultaneous ingestion of a non-steroidal anti-inflammatory compound.

16. The composition of claim 11 wherein the non-steroidal anti-inflammatory is selected from the group consisting of aspirin, acetaminophen, ibuprofen, piroxicam, naproxen, flufenamic and methanamic acid and related nonsteroidal antiinflammatory compounds.

* * * * *